United States Patent
Valteau et al.

(10) Patent No.: US 9,289,269 B2
(45) Date of Patent: Mar. 22, 2016

(54) LIGHTING DEVICE FOR FORMING AN ILLUMINATION SPOT OF VARIABLE DIAMETER AND OF VARIABLE COLOR TEMPERATURE

(71) Applicant: MAQUET SAS, Ardon (FR)

(72) Inventors: Cécilia Valteau, Ligny le Ribault (FR); Minh Hong Vu Thi, Orleans (FR)

(73) Assignee: MAQUET SAS, Ardon (FR)

( * ) Notice: Subject to any disclaimer, the term of this patent is extended or adjusted under 35 U.S.C. 154(b) by 56 days.

(21) Appl. No.: 14/251,065

(22) Filed: Apr. 11, 2014

(65) Prior Publication Data
US 2014/0328045 A1 Nov. 6, 2014

(30) Foreign Application Priority Data
May 3, 2013 (FR) ...................... 13 54082

(51) Int. Cl.
| | |
|---|---|
| *F21V 7/00* | (2006.01) |
| *A61B 19/00* | (2006.01) |
| *F21V 13/04* | (2006.01) |
| *F21V 19/02* | (2006.01) |
| *F21W 131/205* | (2006.01) |
| *F21Y 101/02* | (2006.01) |

(Continued)

(52) U.S. Cl.
CPC ........... *A61B 19/5202* (2013.01); *F21V 7/0033* (2013.01); *F21V 13/04* (2013.01); *F21V 19/02* (2013.01); *A61B 2019/521* (2013.01); *F21W 2131/205* (2013.01); *F21Y 2101/02* (2013.01); *F21Y 2111/001* (2013.01); *F21Y 2113/002* (2013.01)

(58) Field of Classification Search
CPC .. A61B 19/5202; F21S 8/00; F21W 2131/20; F21W 2131/202; F21W 2131/205
USPC .......................................... 362/298; 359/494
See application file for complete search history.

(56) References Cited

U.S. PATENT DOCUMENTS

| | | | | |
|---|---|---|---|---|
| 4,893,223 A | * | 1/1990 | Arnold | ............................ 362/11 |
| 7,325,957 B2 | * | 2/2008 | Morejon et al. | ............... 362/555 |

(Continued)

FOREIGN PATENT DOCUMENTS

| | | |
|---|---|---|
| DE | 10 2006 040 393 | 3/2008 |
| EP | 2 299 163 | 3/2011 |

OTHER PUBLICATIONS

Search Report from French Application No. 1354082 mailed Nov. 14, 2013.

*Primary Examiner* — Evan Dzierzynski
*Assistant Examiner* — Matthew Peerce
(74) *Attorney, Agent, or Firm* — Merchant & Gould P.C.

(57) ABSTRACT

A lighting device comprises a first light source (10) at a first color temperature (Tk1), a second light source (20) at a second color temperature (Tk2) that is different from the first color temperature, and an optical system that forms an illumination spot (3) at an intermediate color temperature (Tkr). The optical system comprises a beam splitter (13) that is arranged to split the light produced by each light source (10, 20) into a transmitted light beam and a reflected light beam. It is arranged to focus said transmitted and reflective light beams (FR1, FR2) and to combine them in a certain superposition configuration in a superposition plane in which said illumination spot is formed, and the optical system and the light sources are arranged to modify the size of the illumination spot (3) at said intermediate temperature.

14 Claims, 6 Drawing Sheets

(51) Int. Cl.
*F21Y 111/00* (2006.01)
*F21Y 113/00* (2006.01)

(56) References Cited

U.S. PATENT DOCUMENTS

| | | | |
|---|---|---|---|
| 7,367,687 B2* | 5/2008 | Cheng | 362/247 |
| 7,465,065 B2 | 12/2008 | Marka | |
| 7,982,954 B2* | 7/2011 | Schuck et al. | 359/489.07 |
| 8,042,972 B2* | 10/2011 | Joergensen et al. | 362/268 |
| 2006/0007538 A1* | 1/2006 | Robinson | 359/494 |
| 2006/0164726 A1 | 7/2006 | Morejon et al. | |
| 2007/0138966 A1 | 6/2007 | Marka et al. | |
| 2008/0174868 A1 | 7/2008 | Schuck et al. | |
| 2010/0039796 A1* | 2/2010 | Mukawa | 362/97.1 |
| 2010/0045896 A1* | 2/2010 | Shikii et al. | 349/62 |
| 2011/0069485 A1 | 3/2011 | Jacobi | |
| 2011/0075420 A1* | 3/2011 | Van Gorkom et al. | 362/235 |
| 2013/0094215 A1* | 4/2013 | Jurik et al. | 362/296.01 |
| 2014/0268063 A1* | 9/2014 | Akiyama et al. | 353/20 |

\* cited by examiner

LIGHTING DEVICE FOR FORMING AN ILLUMINATION SPOT OF VARIABLE DIAMETER AND OF VARIABLE COLOR TEMPERATURE

This application claims benefit of Ser. No. 13/540,82, filed 3 May 2013 in France and which application is incorporated herein by reference. To the extent appropriate, a claim of priority is made to the above disclosed application.

TECHNICAL FIELD

The invention relates to a lighting device, in particular for illuminating a medical operative field.

PRIOR ART

In a medical environment, and in particular in an operating theater, the lighting conditions should be appropriate for enabling the user, e.g. a surgeon or a physician, to work properly. In particular, the illumination should be as homogeneous as possible so that the user can distinguish between the various types of tissue lying within the illumination spot. In addition, the light, which is generally white, should comply with certain standards and should have a color rendering index (CRI) lying in the range 85 to 100, and a color temperature lying in the range 3000 Kelvin (K) to 6700 K. In addition, it is often desirable for it to be possible for the user to vary certain spectral characteristics of the light, including color temperature, so as to adapt them to suit the user's needs. Ideally, such a variation in spectral characteristics should not be accompanied by any variation in the visual illumination. Finally, it is often useful to have an illumination spot that is of variable size.

Currently, there exist various types of lighting device that satisfy these requirements at least in part, and that mix the light coming from a plurality of light sources so as to obtain a white-light illumination.

For example, Patent EP 2 299 163 discloses a lighting device provided with two series of light-emitting diodes (LEDs) that are white and of respective different color temperatures, namely warm white and cool white, distributed in alternation around the periphery of a central reflector that focuses the light emitted by the LEDs so as to form the illumination spot. The resulting color temperature of that lighting device can be modified. However, the resulting light volume is not homogeneous. In addition, when a user looks at that lighting device, alternating color temperatures can be seen, which gives rise to visual discomfort.

Patent Document U.S. Pat. No. 7,465,065 also discloses a lighting device having white and colored LEDs that are juxtaposed to obtain light that is white overall. However, such a lighting device produces light that is not homogeneous. In addition, when an obstacle masks some fraction of the light flux, e.g. when the user leans under the lighting device, the equilibrium between the contributions of the various LEDs is distorted, which modifies the color temperature and gives rise to an iridescent effect leading to colored shadows being formed in the illumination spot. In addition, that lighting device does not make it possible to vary the dimensions of the illumination spot.

Patent Document DE 10 2006 040 393 also discloses a lighting device including white and colored lights coupled together to a single focusing system making it possible to obtain white light of adjustable color temperature. In order to improve the mixing of the colors, a light guide is interposed between the LEDs and a focusing system. However, such a light guide reduces the optical efficiency of the lighting device, resulting in high electrical power consumption.

Patent Documents US 2008/17468 and US 2006/164726 disclose devices for projecting light on a screen with colored LEDs coupled to an optical system. However, since those devices use color LEDs, a color temperature cannot be attributed to them. In addition, those devices do not appear to enable the size of the illumination zone to be modified.

SUMMARY OF THE INVENTION

An object of the invention is thus to remedy those drawbacks by proposing a lighting device offering homogeneous illumination, and high optical efficiency, without creating colored shadows in the field of illumination, and while allowing the size of the illumination spot to be varied and allowing the illumination color temperature to be varied.

To this end, the invention provides a lighting device for illuminating an operative field, the lighting device comprising a first light source suitable for emitting a first light beam at a first color temperature, a second light source suitable for emitting a second light beam at a second color temperature that is different from the first color temperature, and an optical system that uses the light from the sources to form an illumination spot at an intermediate color temperature lying between the first color temperature and the second color temperature, said lighting device being characterized in that the optical system comprises a beam splitter that is arranged to split the light produced by each light source into a transmitted light beam and a reflected light beam, in that the optical system is arranged to focus the reflected second light beam portion of said first light beam together with the transmitted first light beam portion of said second light beam so as to form a first resulting beam having said intermediate color temperature, and to focus the transmitted first light beam portion of said first light beam together with the reflected second light beam portion of said second light beam so as to form a resulting second beam having the same said intermediate color temperature, and to combine them in a certain superposition configuration in a superposition plane in which said illumination spot is formed at an intermediate color temperature, and in that the optical system and the light sources are arranged to modify the size of the illumination spot at said intermediate temperature.

In conventional manner, the diameter D10 of a generally circular illumination spot corresponds to the diameter of the illumination spot at 10% of the maximum illumination of the same illumination spot measured at one meter (m) from the illumination.

In a preferred embodiment of the invention, the size of the illumination spot may vary from a small diameter D10, e.g. 10 centimeters (cm) to a large diameter D10, e.g. 20 cm, and the variation in the diameter of the illumination spot is achieved without any mechanical movement in the lighting device.

In other embodiments of the invention, the variation in the diameter of the illumination spot may be obtained by a movement of the light sources relative to the beam splitter in the lighting device, or indeed by a movement of the optical system relative to the beam splitter in the lighting device, or by a combination of different movements of the sources and of the optical system relative to the beam splitter.

The variation in the color temperature of the illumination spot is obtained by controlling the magnitudes of the feed currents in the light sources.

The lighting device of the invention may advantageously have the following features:

said light sources may be white LEDs;

said light sources may comprise first LEDs that are disposed at a first distance from the beam splitter and second LEDs that are disposed at a second distance from the beam splitter that is different from said first distance; the LEDs at the first distance from the beam splitter serve to form a small illumination spot, while the LEDs at the second distance from the beam splitter serve to form a larger illumination spot; with this arrangement, it is possible to modulate the diameter of the illumination spot without any mechanical movement in the lighting device, and in particular with light sources that are static relative to the beam splitter, thereby simplifying the construction of the lighting device while also keeping the lighting constant by controlling the magnitudes of the feed currents in the light sources;

said first LEDs disposed at the first distance from the beam splitter comprise a first ring of LEDs having said first color temperature and a second ring of LEDs having said second color temperature, and said second LEDs disposed at the second distance from the beam splitter comprise a third ring of LEDs having said first color temperature and a fourth ring of LEDs having said second color temperature, said first and third rings of LEDs being offset from each other along an illumination axis of the lighting device, and said second and fourth rings of LEDs being offset from each other along a direction that is radial relative to said illumination axis; this arrangement contributes to obtaining an illumination spot that is central to an illumination axis of a lighting dome with the possibility of varying the diameter of the spot without any mechanical movement in the lighting;

the LEDs of the first and the third rings of LEDs are disposed in alternation relative to one another by defining a sort of crenellation along the illumination axis, and the LEDs of the second and fourth ring of LEDs are disposed in alternation relative to one another by defining a sort of crenellation in the radial direction; this arrangement of the LEDs makes it possible for the LEDs to be mounted compactly in a lighting dome;

an electrical power supply is provided for feeding currents to the LEDs, and for modulating the currents so as to cause a modification in the size of the illumination spot, and/or a modification in the color temperature of the illumination spot;

the electrical power supply is further arranged to modulate said currents in such a manner as to form an illumination spot at a constant illumination level;

said light sources may also comprise LEDs that are mounted to move relative to the beam splitter; such an arrangement also makes it possible to modify the size of the illumination spot;

the optical system comprises an elliptical reflector and a lens for focusing said transmitted and said reflected light beams, and said elliptical reflector may be mounted to move relative to the beam splitter and/or said lens may be mounted to move relative to the beam splitter; this also makes it possible to modify the size of the illumination spot;

the elliptical reflector may be a faceted reflector, thereby making it possible to increase the depth of the field of illumination, and also the shadow dilution performance of the dome;

the optical system may further comprise a mirror disposed to deflect the light produced by a light source through 90° towards the beam splitter, thereby contributing to the compactness of the lighting device; lenses may also be provided in front of each LED so as to collect a maximum amount of light flux coming from the LED with a smaller solid angle; and the beam splitter may be a semi-reflective mirror angularly positioned at 45° relative to the light sources or LEDs.

BRIEF DESCRIPTION OF THE DRAWINGS

The present invention can be better understood and other advantages appear on reading the following detailed description of embodiments given by way of non-limiting example and with reference to the accompanying drawings, in which.

DESCRIPTION OF AN EMBODIMENT

Figure 1:
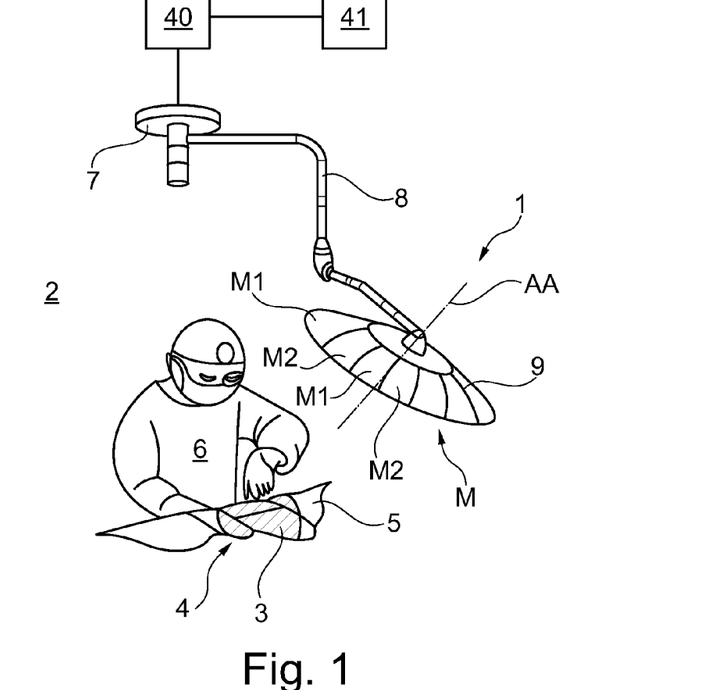
FIG. 1 is a perspective view of a lighting device of the invention that is used in an operating theater.

With reference to FIG. 1, the lighting device 1 of the invention is, in particular, designed to be used in an operating theater 2 for forming an illumination spot 3 (shown diagrammatically by shading) in an operative field 4, e.g. on the body of a patient 5 being operated on by a surgeon 6. In this example, and in known manner, the lighting device 1 has a base 7 that is fastened to the ceiling of the operating theater 2 and from which an articulated arm 8 extends that carries a lighting dome 9 in which there are disposed, for example, a plurality of lighting modules M, provided in this example with LEDs (not shown in this figure), each of which modules, in this example, is in the form of a quarter of the dome so as to deliver an illumination spot 3 that is centered on the illumination axis AA of the dome.

The lighting device 1 of the invention is designed to form an illumination spot 3 of variable size and of variable color temperature using the light modules M, each light module having two light sources having different color temperatures, e.g. two white LEDs disposed symmetrically relative to a beam splitter. More particularly, said illumination spot is formed by superposing illuminations that are centered on the axis AA and that are produced by the different light modules M.

Figure 2:
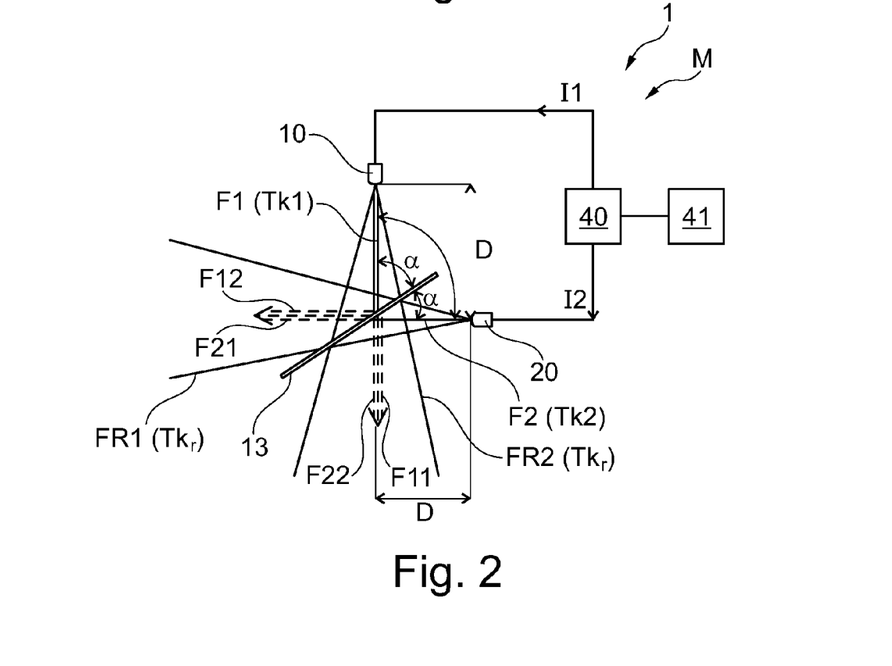
FIG. 2 is a diagram showing how the beam splitter is mounted.

FIG. 2 shows the principle of splitting the light beams produced by two LEDs 10, 20 in a light module M. The first LED 10 is suitable for emitting a first light beam F1 (shown diagrammatically by a double uninterrupted line) having a first color temperature Tk1. The second LED 20 is suitable for emitting a second light beam F2 (shown diagrammatically by a single uninterrupted line) having a second color temperature Tk2 that is different from the first color temperature Tk.

Preferably, the first and second LEDs 10, 20 that are used are geometrically identical and have different color temperatures Tk1, Tk2, and they come from the same supplier, have the same housings, have the same electronic chips, and require the same type of power supply. It is thus possible to limit the effects of any difference in light flux between the first and second LEDs 10 and 20, in order to guarantee homogeneous illumination.

In order to obtain lighting that is suitable for a medical environment, white LEDs 10, 20 are chosen that are of high color rendering index, lying in the range 85 to 100, and preferably in the range 90 to 100, or indeed lying in the range 95 to 100, and that are of color temperature Tk1, Tk2 lying in the range 3000 K to 5000 K. By way of example, it is possible to use an LED 10 having a first color temperature Tk1 of 3000 K, and an LED 20 having a second color temperature Tk2 of 5000 K. Thus, when first and second electric currents I1, I2 that are of substantially identical magnitude flow through respective ones of the LEDs 10, 20, if the first and second beams F1, F2 are superposed, white-light illumination is obtained that has an intermediate color temperature Tkr of about 4000 K.

In FIG. 2, the first and second LEDs 10, 20 are angularly positioned so that the median axes of the beams F1, F2 are angularly positioned at 90° relative to each other, and it can be understood that said LEDs are disposed symmetrically relative to the beam splitter 13.

For example, the beam splitter 13 is a high-efficiency dichroic or semi-reflective mirror that is spectrally neutral and that includes a backing plate (made of glass or of a synthetic material) covered with a plurality of layers having optical treatments. The beam splitter 13 is suitable for splitting each of the first and second beams F1, F2 into a first beam portion F11, F21 (shown diagrammatically respectively by a uninterrupted double line and by a uninterrupted single line) that is transmitted by the beam splitter 13, and into a second beam portion F12, F22 (diagrammatically shown by a dashed double line and by a dashed single line) that is reflected by the beam splitter 13. Preferably, the beam splitter 13 that is used makes it possible to split each beam F1, F2 with a theoretical efficiency of 100%, i.e. without any loss, comprising, for example, 50% in reflection and 50% in transmission, or, for example, 30% in reflection and 70% in transmission.

The beam splitter 13 is disposed at equal distance D from the LEDs 10, 20 and forms the same angle α of 45° with each of the beams F1, F2. In addition, the beam splitter 13 and the LEDs 10, 20 are arranged three-dimensionally so that the first beam F1 and the second beam F2 reach the beam splitter 13 opposite from each other, on either side of the beam splitter 13. Thus, the second portion F12 of the first beam F1 is superposed on or is combined with said first portion F21 of the second beam F2 so as to form a first resulting beam FR1 having a resulting intermediate color temperature Tkr that lies between the first and second color temperatures Tk1, Tk2. In addition, the first portion F11 of the first beam F1 is superposed on or is combined with said second portion F22 of the second beam F2 so as to form a second resulting beam FR2 having the same resulting color temperature Tkr.

Figure 4A:
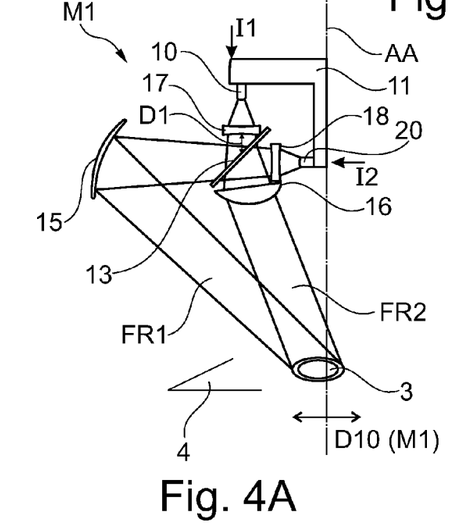
FIG. 4A is a diagram of an optical system and of the light sources for forming a "small illumination spot"
Figure 4B:
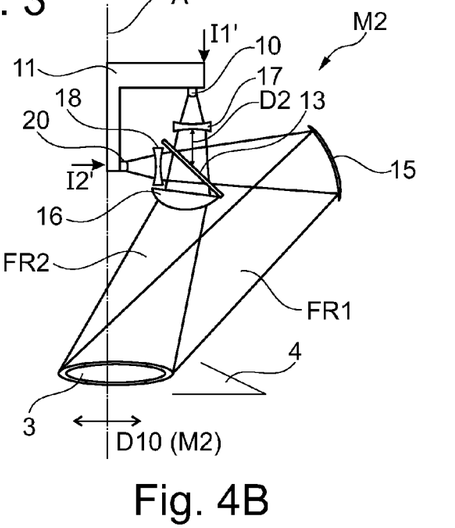
FIG. 4B is a diagram of an optical system and of the light sources for forming a "large illumination spot"

Although not shown in FIG. 2 (but visible in FIG. 4), each LED 10, 20 is equipped with a lens that serves to collimate the light produced by the LED onto the splitter 13, the assembly comprising the LED 10 and its lens, and the assembly comprising the LED 20 and its lens being symmetrical about the splitter 13 and being placed respectively at equal distance D therefrom.

The light module M thus makes it possible to produce, at a certain color temperature Tkr, a total light flux equal to the sum of the respective light fluxes of the first and second LEDs 10, 20.

The LEDs 10, 20 of each lighting module M are connected electrically to an electrical power supply 40 coupled to a monitoring and control unit (MCU) 41 suitable for controlling the electrical power supply 40 so as to power the first LED 10 with a first electric current I1 and so as to power the second LED 20 with a second electric current I2 that may be different from I1, thereby making it possible to cause the color temperature to vary.

The electrical power supply 40 may be in the form of a single electrical power supply for all of the LEDs of the modules M or in the form of two distinct electrical power supplies selectively and respectively feeding all of the LEDs 10 and all of the LEDs 20. It is known that the light flux from an LED depends on the magnitude of the current that is passing through it. In order to modulate the color temperature, the electrical power supply 40 is controlled by the MCU 41 in such a manner as to modulate the magnitude of the first and second electric currents I1, I2 on the principle of communicating vessels, as shown in FIG. 20, i.e. in substantially complementary and opposite manner.

Figure 20:
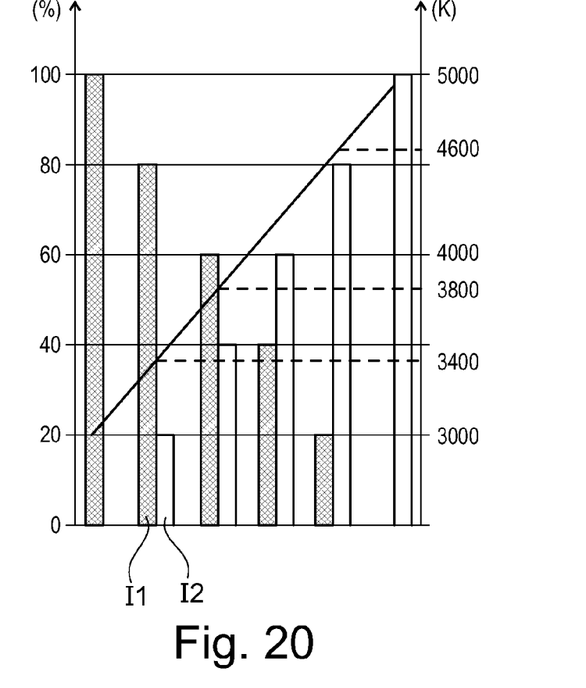
FIG. 20 is a graph that, for different adjustment settings in percentage (%) for the magnitudes of the first and second currents fed to the LEDs, shows the variation in the resulting color temperature in K.

FIG. 20 shows six distinct power supply configurations for feeding with electric currents I1, I2. In a first power supply configuration, and in a module M, the LED 10 is powered with 100% of the electric current I1 and the LED 20 is powered with 0% of the current I2. Thus, only the LED 10 is used, and the resulting color temperature Tkr corresponds to the first color temperature Tk1 of the LED 10, which, in this example, is 3000 K. In a second power supply configuration, the LED 10 is powered with 80% of the electric current I1 and the LED 20 is powered with 20% of the current I2. The corresponding resulting color temperature Tkr lies between the first and second color temperatures Tk1, Tk2, and, in this example, is 3400 K. The currents I1, I2 may be further modulated until up to a sixth power supply configuration is reached in which the LED 10 is powered with 0% of the electric current I1 and the LED 20 is powered with 100% of the current I2. The resulting color temperature Tkr corresponds to the color temperature Tk2 of the LED 10, which, in this example, is 5000 K.

Thus, with a light module M, it is possible to form an illumination spot 3 with a variable color temperature lying in the range Tk1 to Tk2.

Figure 3:
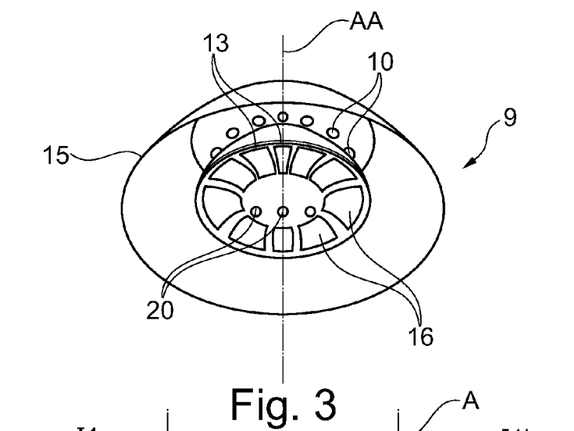
FIG. 3 is a diagrammatic perspective view of the optical system of a lighting device of the invention.

In the dome 9, it can be understood that there are provided a plurality of light modules M distributed about the illumination axis AA so that the LEDs 10 of the light modules M form a first ring about the illumination axis AA, and the LEDs 20 of said light modules M form a second ring about the axis AA so that the two rings are on the same axis. The first ring of LEDs 10 has a diameter greater than the diameter of the second ring of LEDs 20. It can also be understood that, in the dome 9, there thus exist a series of beam splitters 13 distributed about the illumination axis AA and that also form a ring of beam splitters on the same axis as the rings of LEDs 10, 20, as shown in FIG. 3.

In accordance with the invention, the above-described construction principle of the lighting module M is used for implementing a lighting device 1 that is, in particular, in the form of a dome and with which it is possible to form an illumination spot 3 that is, in addition, of variable size in the working plane that corresponds to the operative field 4 that is about 1 meter (m) away from the dome.

In a preferred embodiment, first light modules M1 having LEDs 10, 20 dedicated to forming a small illumination spot, e.g. a spot having a diameter of 10 centimeters (cm), are used, and second light modules M2 having LEDs 10, 20 dedicated to forming a larger illumination spot, e.g. having a diameter of 20 cm, are used, and an electrical power supply is used that adjusts the currents for feeding to the LEDs in the light modules so as to modify the size of the illumination spot 3.

FIGS. 4A and 4B are highly diagrammatic views respectively showing a light module M1 having LEDs 10, 20 dedicated to forming a small illumination spot 3 centered on the illumination axis AA of the dome, and a light module M2 having LEDs 10, 20 dedicated to forming a large illumination spot 3 centered on the illumination axis AA.

In the light module M1 of FIG. 4A, the LEDs 10, 20 are placed at a distance D1 from the splitter 13. In the light module M2 of FIG. 4B, the LEDs 10, 20 are placed at a distance D2 from the splitter 13, where D2 is different from D1 and, in this example, greater than D1 (but it is also possible to have D2 smaller than D1 in order to optimize the compactness of the dome). The reference 11 designates a support to which the LEDs 10, 20 are fastened in the dome 9.

FIGS. 4A and 4B also show each LED 10 with a lens 17 for collimating the light beam F1 onto the splitter 13, and also show each LED 20 with a lens 18 for collimating the light beam F2 onto the splitter 13. These lenses 17, 18 are identical and they are placed at the same distance from their respective LEDs 10, 20. For example, they are biconcave lenses that are suitable for reducing the divergence of the light beams F1, F2, thereby contributing to the compactness of the lighting dome 9. It should be noted that these lenses should always be placed at the same distance from the respective LEDs.

As also shown in FIGS. 4A and 4B, each light module M1, M2 has an optical system that comprises a reflector 15 and a lens 16, the reflector being, in this example, an elliptical reflector, said reflector and said lens serving to form the illumination spot 3 in the working plane from the incident light beams F12, F21, F11, F22 (shown in FIG. 2).

Figure 5:
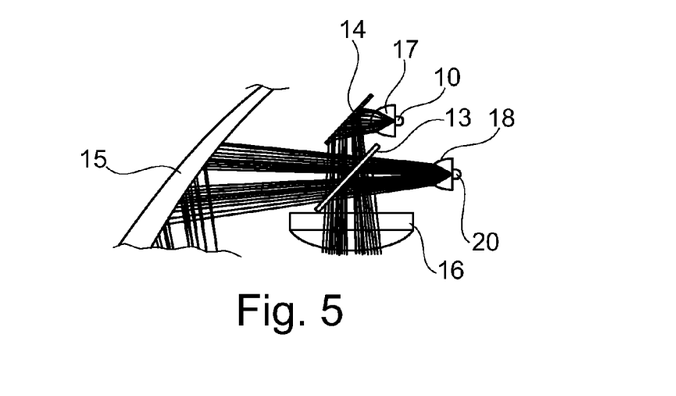
FIG. 5 is a diagram showing the light sources and the optical system in a compact configuration of the lighting device of the invention.

FIG. 5 shows a compact arrangement for the lighting device 1 of the invention, in which arrangement, in each module M, a mirror 14 is interposed between the beam splitter 13 and the lens of the LED 10 so as to force the beam F1 to make a right angle. With this three-dimensional arrangement, it is possible to save space in the height direction in the dome 9 and thus to improve the compactness thereof.

In the light module M1 dedicated to forming a small illumination spot 3 there exists the virtual image of the LED 10 (as a result of the lens 17) that corresponds to the object focal point of the lens 16, and the virtual image of the LED 20 (as a result of the lens 18) that corresponds to the object focal point of the reflector 15. The arrangement of the light module M1 is thus suitable for producing a small illumination spot 3 in the working plane by combining focusing (beam narrowing) and superposition of the light beams FR1 and FR2 coming from the reflector 15 and from the lens 16.

Now, as appears in FIG. 4B, due to the distance D2 being different from D1, this correspondence between virtual image and focal point in the light module M2 no longer exists, but rather, in said light module M2 there exists a virtual image of the LED 10 that is offset from the object focal point of the lens 16, and a virtual image of the LED 20 that is offset from the object focal point of the reflector 15. The arrangement of the light module M2 is thus suitable for producing a large illumination spot 3 (i.e. a spot that is larger than the spot produced by the module M1) in the working plane by combining defocusing (beam widening) and superposition of the light beams FR1 and FR2 coming from the reflector 15 and from the lens 16.

In a lighting device of the invention in the form of a lighting dome, in practice the modules M1 and M2 are disposed in alternation about the illumination axis AA. Disposed in the dome are a series of reflectors 15 of the modules M1 and M2 that are distributed about the illumination axis AA and that form a sort of ring on the same axis as the rings of LEDs 10, 20, and a series of lenses 16 of said modules M1 and M2 that are also distributed about the illumination axis AA and that form another ring that is on the same axis as the rings of LEDs, as shown in FIG. 3.

By means of the MCU 41, the electrical power supply 40 is controlled in such a manner as selectively to send currents I1, I2 respectively into the LEDs 10, 20 of the light modules M1 and currents I1', I2' respectively into the LEDs 10, 20 of the light modules M2 so as to modify the size of the illumination spot and/or so as to modify the color temperature as described above.

It should be understood that, in this arrangement, in order to keep the color temperature homogeneous in the illumination spot 3 of variable size, each light module M1 and M2 must send the same color temperature. In other words, the ratio I1/I2 should be identical to the ratio I1'/I 2' in order to obtain an illumination spot 3 at the intermediate color temperature Tkr, and said ratio is caused to vary in order to vary the color temperature in the illumination spot over the range Tk1 to Tk2. In order to cause the diameter of the illumination spot to vary, the relative current between the light modules M1 and M2, i.e. the ratio I1/I1', and thus the ratio I2/I2', is caused to vary. For a fixed intermediate color temperature Tkr between Tk1 and Tk2, it is possible to cause I1' and I1 or I2' and I2 to vary on the principle of communicating vessels so as to cause the diameter D10 of the illumination spot to vary between a large diameter (the diameter of the spot produced by the light modules M2 on their own) and a small diameter (the diameter of the spot produced by the light modules M1 on their own). It should be noted that the sum of the currents I1+I1' or I2+I2' must be substantially constant in order to have a variation in illumination spot diameter that is constant, while keeping the ratio I1/I2 equal to I1'/I2' so as to keep the same color temperature in the illumination spot 3.

More particularly, if the currents I1' and I2' are zero, the illumination spot 3 is produced by the light modules M1 on their own only, and so the illumination spot is small, with a diameter, for example, of 10 cm.

If the currents I1 and I2 are zero, the illumination spot 3 is produced by the light modules M2 on their own only, and so the illumination spot is large, with a diameter, for example, of 20 cm.

If non-zero currents I1 and I2 are delivered to the light modules M1 and non-zero currents I1' and I2' are delivered to the light modules M2, an illumination spot is produced with an intermediate diameter between 10 cm and 20 cm.

In order to keep the same level of illumination for the various illumination spot diameters, the MCU 41 adjusts the current in all of the LEDs of the light modules M1 and M2 while keeping the ratio I1'/I2' identical to the ratio I1/I2 in such a manner as not to change the color temperature for the illumination spot 3. In order to go from an illumination spot of a certain diameter to a larger illumination spot, the MCU 41 must increase the currents in the same proportion for each LED.

Figure 16:
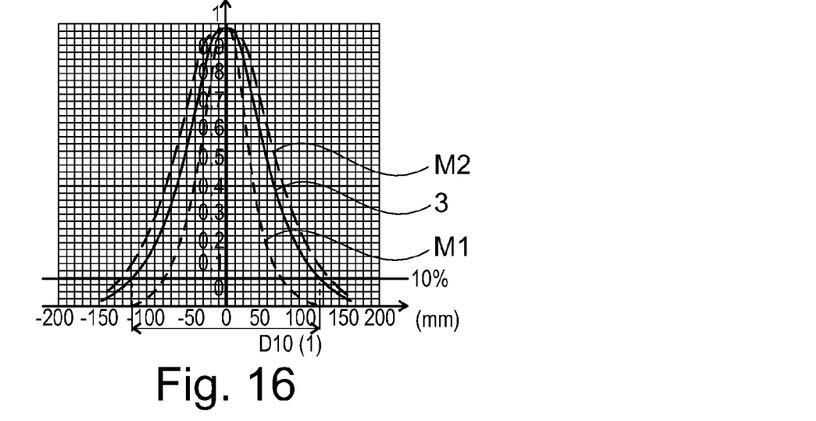
FIGS. 16 to 18 are graphs showing the normalized visual illumination profile as a function of distance to the central axis of the dome for the lighting module of FIG. 4A in the "small spot" configuration (short-dash curves) and for the lighting module of FIG. 4B in the "large spot" configuration (long-dash curves) with the resulting illumination spot (uninterrupted-line curve), as a function of the diameter in millimeters (mm) of the illumination spot.
Figure 17:
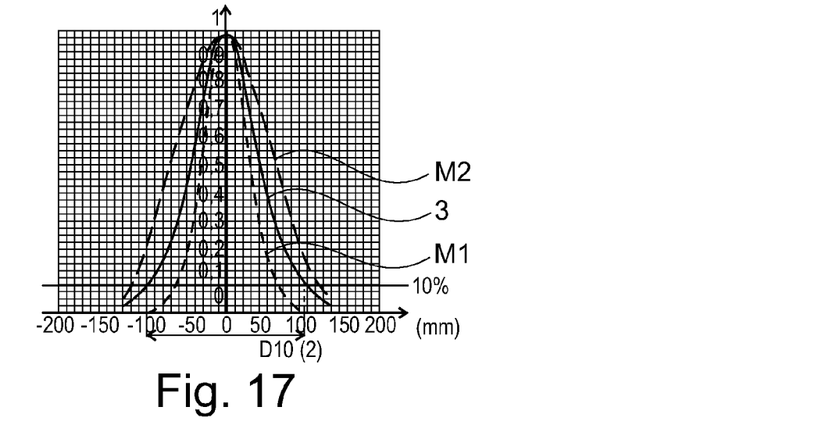
Figure 18:
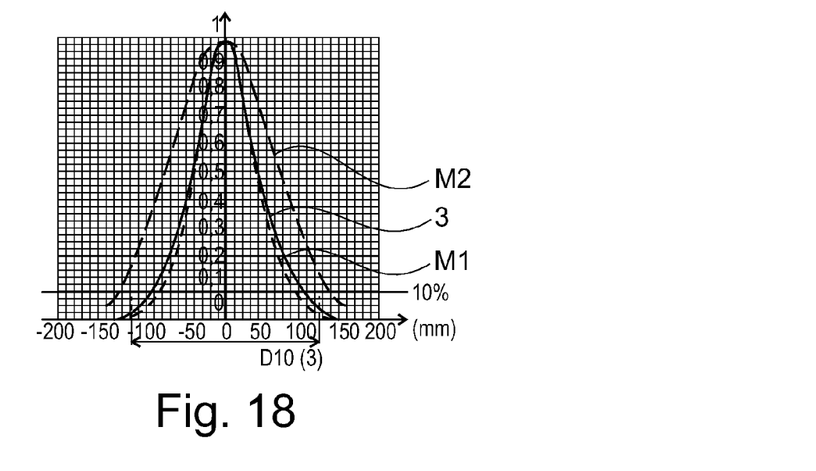

In the graphs of FIGS. 16 to 18, the illumination produced by the modules M1 on their own in the "small spot" configuration is plotted in short dashes. The illumination produced by the modules M2 on their own in the "large spot" configuration is plotted in long dashes. The uninterrupted-line plots represent the superposition of the illuminations produced by the modules M1 and M2.

FIGS. 16 to 18 show how the size of the illumination spot 3 varies as a function of the ratios I1/I1' and I2/I2', in this example with ratios 20/80, 50/50, and 80/20. These ratios can be controlled by the MCU 41 in such a manner as to keep the illumination power constant when the diameter of the illumination spot is changed by the surgeon.

Figure 6:
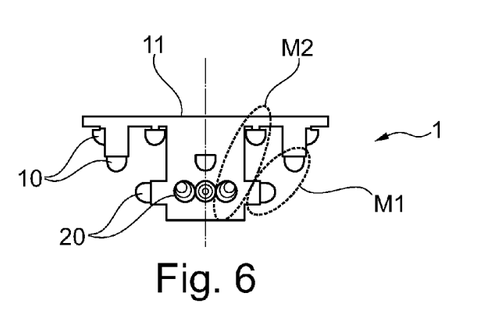
FIGS. 6 and 7 show the particular configuration of the LEDs for enabling the size of the illumination spot to be varied without any mechanical movement being necessary.
Figure 7:
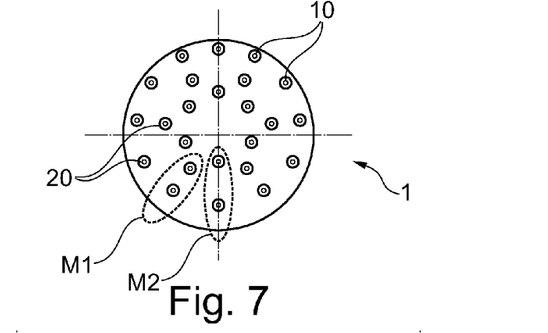

FIGS. 6 and 7 show the relative dispositions of the LEDs 10 and 20 of the modules M1 and M2 on the support 11. It can be seen that LEDs 10 of the modules M1 are disposed in alternation with the LEDs 10 of the modules M2 around the peripheries of the two rings of LEDs 10, thereby forming a sort of crenellation of LEDs in the axial direction of the dome, and it can be seen that the LEDs of the modules M1 are disposed in alternation with the LEDs 20 of the modules M2 around the peripheries of the two rings of LEDs 20, thereby forming another sort of crenellation of LEDs in a radial direction perpendicular to said axial direction.

In the dome 9, the LEDs 10 of the modules M1 and M2 form two rings of LEDs both of which are on the central illumination axis AA, the LEDs 10 in one ring being offset axially relative to the LEDs 10 of the other ring along said central illumination axis. The LEDs 20 of the modules M1 and M2 form two other rings of LEDs both of which are on the illumination axis AA, but the LEDs 20 in one ring are offset radially relative to the LEDs 20 of the other ring.

In the dome 9, there therefore exist two rings of LEDs 10 and 20 that are placed symmetrically relative to the ring of beam splitters 13 and at the distance D1 from said ring of beam splitters, these two rings of LEDs being dedicated to forming a small illumination spot, and two other rings of LEDs 10 and 20 that are placed symmetrically relative to the same ring of beam splitters 13 and at the distance D2 therefrom, these two other rings of LEDs being dedicated to forming the large illumination spot. In this preferred embodiment, it is possible to modify the size and the color temperature of the illumination spot without any mechanical movement in the dome, thereby simplifying manufacture of the dome and increasing its reliability.

In another embodiment of the lighting device of the invention, the LEDs 10, 20 in a light module M are mounted to move relative to the optical system and in particular relative to the beam splitter 13 so as to modify the size of the illumination spot 3. In this embodiment, the dome has a single ring of LEDs 10 (with a lens 17), and a single ring of LEDs 20 (with a lens 18), the two rings of LEDs being constrained to move on the support 11 so as to move together towards or away from the beam splitter 13.

Figure 8:
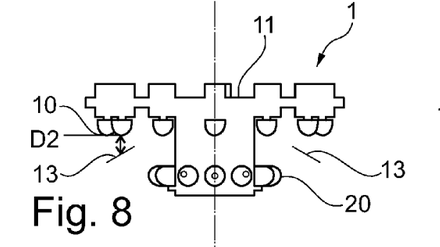
FIGS. 8 to 11 show the configuration of the moving LEDs in the lighting device of the invention for causing the size of the illumination spot to vary.
Figure 9:
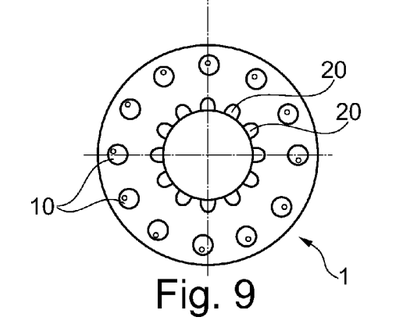

FIGS. 8 and 9 show the two rings of LEDs 10 and 20 that are mounted to move on the support 11 in the dome. In these figures, the LEDs 10, 20 are spaced apart from the beam splitters 13 by a large distance D2 so as to form a large illumination spot 3.

Figure 10:
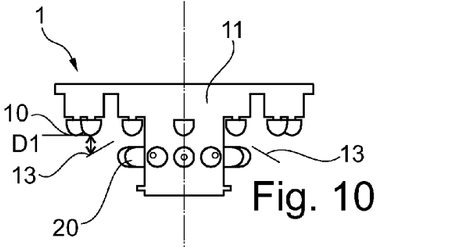
Figure 11:
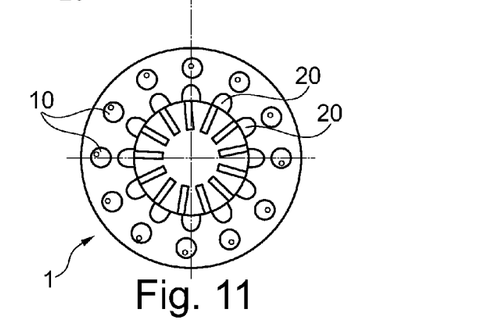

FIGS. 10 and 11 show the same LEDs 10, 20 that have been brought closer together so as to be spaced apart from the beam splitters 13 by the smaller distance D1 so as to form a small illumination spot 3. Naturally, the lenses 17 and 18 move with the LEDs 10 and 20.

The support 11 may be in the form of a disk carrying the LEDs 10 and of a tube disposed on the same axis and carrying the LEDs 20. The relative movement of the LEDs 10 and 20 may be obtained, for example, by telescope sliding of the support tube.

With reference to FIGS. 8 to 11, it is possible to provide an arrangement in which the LEDs 20 are, in addition, mounted to move radially, and the LEDs 10 are, in addition, mounted to move axially. It is thus possible for each LED 10 and 20 (together with its lens 17, 18) to move in two movements in translation, thereby enabling fine adjustment to be made of the distances D1 and D2 and thus of the diameter of the illumination spot 3.

Figure 19:
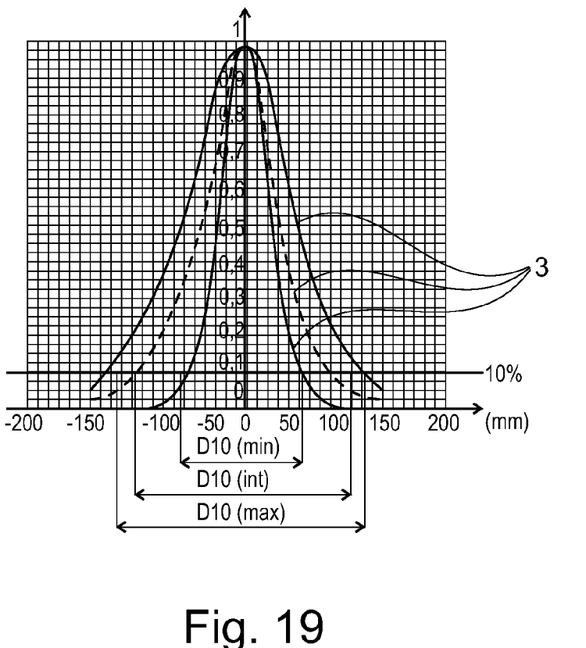
FIG. 19 is a graph showing, on a scale of 0 to 1, the intensity of the visual illumination with the lighting device of FIGS. 8 to 11 in the "small spot" and "large spot" configurations (uninterrupted-line curves) and in an "intermediate" configuration (uninterrupted -line), as a function of the diameter in mm of the illumination spot.

It can be understood that, with a movement of the LEDs 10 and 20 relative to the splitter 13, the light beams FR1 and FR2 produced by the LEDs 10 and 20 are defocused and this results in a variation in the dimension of the illumination spot 3. The graph of FIG. 19 shows other different illumination spots 3 that correspond to different positions for the LEDs 10 and 20 relative to the splitter 13.

It can be understood that in the embodiments of the lighting device shown in FIGS. 6 to 11, the beam splitter 13 may remain stationary in the dome. Naturally, in these embodiments, the MCU 41 controls the currents fed to the LEDs 10, 20 in such a manner as to maintain illumination of constant power regardless of the three-dimensional positions of the LEDs.

Figure 12:
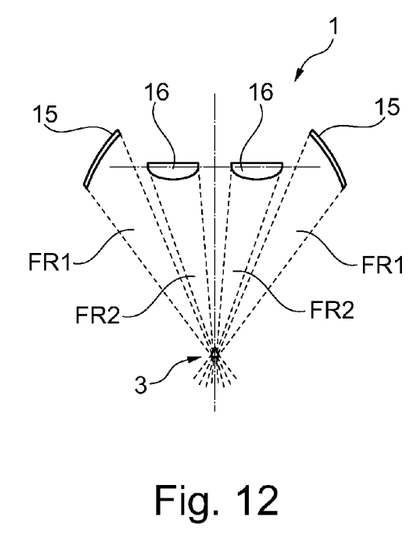
FIGS. 12 and 13 show a lighting device of the invention with an optical system having a moving lens.
Figure 13:
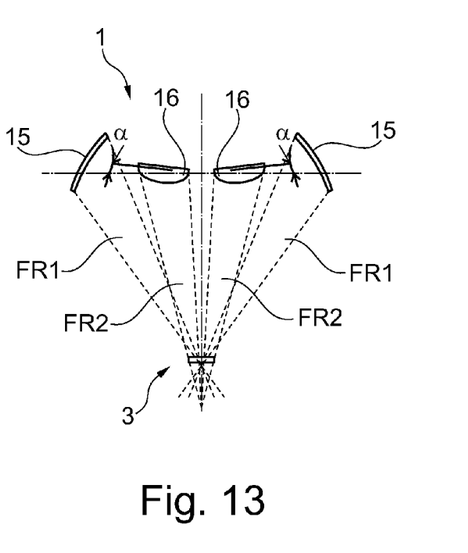

FIGS. 12 and 13 show yet another embodiment of the lighting device for forming an illumination spot of variable size. In this embodiment, a lens 16 is used that that is mounted to move in rotation in the dome so as to pivot through an angle a between a first position in which the beams FR2 are focused and are superposed with the beams FR1 so as to form a small illumination spot (FIG. 12) and a second position in which the focused beams FR2 are offset in the superposition plane, thereby changing the superposition configuration of the beams FR1 and FR2 in the superposition plane so as to form a large illumination spot (FIG. 13). It can be understood that the intermediate angular positions of the lens 16 between the first and second position correspond to as many different sizes for the illumination spot 3.

Figure 14:
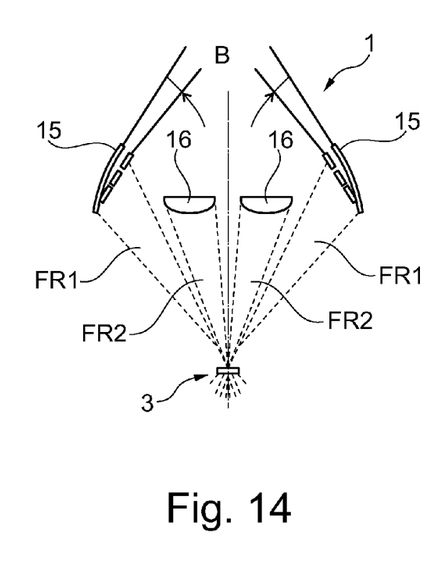
FIG. 14 shows a lighting device of the invention with an optical system having a moving reflector.

FIG. 14 shows yet another embodiment of the lighting device for forming an illumination spot 3 of variable size. In this embodiment, the reflector 15 is mounted to move in rotation in the dome so as to pivot through an angle β between a first angular position (shown in dashed lines) in which the beams FR1 are focused and are superposed with the beams FR2 so as to form a small illumination spot 3 and a second angular position (shown in uninterrupted lines) in which the focused beams FR1 are offset, thereby changing the superposition configuration of the beams FR1 and FR2 in the superposition plane so as to form a large illumination spot 3. It can be understood that the intermediate angular positions of the reflector 15 between the first and second position correspond to as many different sizes for the illumination spot 3.

Figure 15:
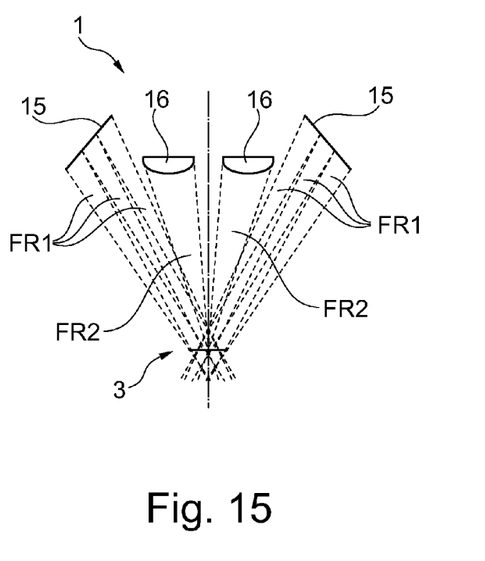
FIG. 15 shows a lighting device of the invention with a faceted reflector.

FIG. 15 shows a faceted elliptical reflector with facets arranged to split the beam FR1 into a plurality of small beams focused at different heights in the central illumination axis AA of the dome 9. This reflector 15 may also be mounted to move in the dome, as indicated above. A faceted reflector 15 makes it possible to increase the depth of the field of illumination.

The lighting device of the invention thus includes light sources, an optical system and a power supply for feeding currents to the light sources, which optical system and which power supply are arranged to place the light beams coming from the sources in different superposition configurations of the light beams in the superposition plane that corresponds to the working plane in which the illumination spot is formed, these various configurations corresponding to different sizes or different diameters of the illumination spot.

Naturally, the present invention is in no way limited to the above description of certain embodiments, which can undergo modifications without going beyond the ambit of the invention. Thus, for example, the illumination spot 3 is not necessarily circular and may, for example be oval.

In addition, the various embodiments of the invention that are presented above may be combined without going beyond the ambit of the invention. It is thus possible, in the dome, to have stationary LEDs and/or moving LEDs with a moving reflector and/or a moving lens.

The invention claimed is:

1. A lighting device for illuminating a medical operative field, the lighting device comprising:
a first white light source suitable for emitting a first light beam at a first color temperature;
a second white light source suitable for emitting a second light beam at a second color temperature that is different from the first color temperature; and
an optical system that uses the light from the light sources to form an illumination spot at an intermediate color temperature lying between the first color temperature and the second color temperature, said optical system comprises a fixed beam splitter arranged to split light produced by each of the first and second light sources into a transmitted light beam portion and a reflected light beam portion; wherein the optical system is arranged to focus the reflected second light beam portion of said first light beam together with the transmitted first light beam portion of said second light beam to form a first resulting beam having said intermediate color temperature, and to focus the transmitted first light beam portion of said first light beam together with the reflected second light beam portion of said second light beam to form a second resulting beam having said intermediate color temperature, and to combine said first resulting beam and said second resulting beam in a superposition configuration to form said illumination spot at said intermediate color temperature in a superposition plane of said medical operative field; and wherein said optical system and said light sources are arranged to modify the size of the illumination spot at said intermediate color temperature.

2. A lighting device according to claim 1, wherein said light sources comprise first LEDs that are disposed at a first distance from said fixed beam splitter and second LEDs that are disposed at a second distance from said fixed beam splitter that is different from said first distance.

3. A lighting device according to claim 2, wherein said first LEDs disposed at the first distance from the beam splitter comprise a first ring of LEDs having said first color temperature and a second ring of LEDs having said second color temperature, in that said second LEDs disposed at the second distance from the beam splitter comprise a third ring of LEDs having said first color temperature and a fourth ring of LEDs having said second color temperature, in that said first and third rings of LEDs are offset from each other along an illumination axis of the lighting device, and in that said second and fourth rings of LEDs are offset from each other along a direction that is radial relative to said illumination axis.

4. A lighting device according to claim 3, wherein the LEDs of the first and the third rings of LEDs are disposed in alternation relative to one another along the illumination axis, and in that the LEDs of the second and fourth ring of LEDs are disposed in alternation relative to one another in the radial direction.

5. A lighting device according to claim 2, wherein it further comprises an electrical power supply for feeding currents to the LEDs and for modulating the currents so as to cause a modification in the size of the illumination spot, and/or a modification in the color temperature of the illumination spot.

6. A lighting device according to claim 5, wherein the electrical power supply is arranged to modulate said currents in such a manner as to form the illumination spot at a constant illumination level.

7. A lighting device according to claim 1, wherein said light sources comprise LEDs mounted to move relative to the fixed beam splitter.

8. A lighting device according to claim 1, wherein said fixed beam splitter is a semi-reflective mirror angularly positioned at 45° relative to said light sources.

9. A lighting device according to claim 1, wherein the optical system comprises an elliptical reflector and a lens for focusing said transmitted light beam and said reflected light beams.

10. A lighting device according to claim 9, wherein said elliptical reflector is mounted to move relative to the fixed beam splitter.

11. A lighting device according to claim 9, wherein said elliptical reflector is a facetted reflector.

12. A lighting device according to claim 9, wherein said lens is mounted to move relative to the fixed beam splitter.

13. A lighting device according to claim 1, wherein the optical system further comprises a mirror disposed to deflect light produced by one of the light sources through 90° towards the fixed beam splitter.

14. A lighting device according to claim 1, wherein said light sources are white LEDs.

* * * * *